US007470319B2

(12) United States Patent
Hunter et al.

(10) Patent No.: US 7,470,319 B2
(45) Date of Patent: Dec. 30, 2008

(54) COMPOSITION AND METHOD FOR CROP PROTECTION

(75) Inventors: Gregory S. Hunter, Kiowa, CO (US); Carl W. Nichols, Bozeman, MT (US)

(73) Assignee: Luzenac America, Inc., Greenwood Village, CO (US)

( * ) Notice: Subject to any disclaimer, the term of this patent is extended or adjusted under 35 U.S.C. 154(b) by 273 days.

(21) Appl. No.: 10/929,344

(22) Filed: Aug. 27, 2004

(65) Prior Publication Data
US 2005/0085386 A1  Apr. 21, 2005

Related U.S. Application Data

(60) Provisional application No. 60/499,055, filed on Aug. 29, 2003.

(51) Int. Cl.
C09C 1/42 (2006.01)

(52) U.S. Cl. ...................................... 106/469

(58) Field of Classification Search ................ 504/120, 504/121, 123, 119; 47/2, DIG. 11; 106/469
See application file for complete search history.

(56) References Cited

U.S. PATENT DOCUMENTS

| | | | | |
|---|---|---|---|---|
| 2,624,663 | A * | 1/1953 | Centanni | 504/101 |
| 3,586,478 | A | 6/1971 | Neumann | |
| 4,118,246 | A | 10/1978 | Horzepa et al. | |
| 4,144,083 | A * | 3/1979 | Abercrombie, Jr. | 501/146 |
| 4,186,027 | A | 1/1980 | Bell et al. | |
| 4,267,065 | A | 5/1981 | Johnson, Jr. et al. | |
| 4,309,222 | A | 1/1982 | Hoyt, IV | |
| 4,374,203 | A | 2/1983 | Thompson et al. | |
| 4,650,521 | A | 3/1987 | Koppelman et al. | |
| 4,780,147 | A | 10/1988 | Ou et al. | |
| 5,342,630 | A * | 8/1994 | Jones | 424/717 |
| 5,424,259 | A | 6/1995 | Yordan et al. | |
| 5,543,372 | A | 8/1996 | Shi et al. | |
| 5,707,912 | A | 1/1998 | Lowe et al. | |
| 5,908,708 | A | 6/1999 | Sekutowski et al. | 428/541 |
| 6,027,740 | A | 2/2000 | Puterka et al. | 424/405 |
| 6,069,112 | A * | 5/2000 | Glenn et al. | 504/119 |
| 6,074,473 | A * | 6/2000 | Nichols et al. | 106/469 |
| 6,110,867 | A * | 8/2000 | Glenn et al. | 504/119 |
| 6,136,740 | A | 10/2000 | Jones et al. | |
| 6,156,327 | A | 12/2000 | Sekutowski et al. | 424/405 |
| 6,284,099 | B1 | 9/2001 | Peutherer et al. | |
| 6,309,440 | B1 * | 10/2001 | Yamashita | 71/27 |
| 6,555,633 | B1 | 4/2003 | Tanka et al. | |
| 6,877,275 | B2 | 4/2005 | Glenn et al. | |
| 2003/0159349 | A1 | 8/2003 | Glenn et al. | |

OTHER PUBLICATIONS

U.S. Appl. No. 10/931,280, Nichols, filed Aug. 30, 2004.

Abou-Khaled et al.;1970; "Effects of Kaolinite as a Reflective Antitranspirant on Leaf Temperature, Transpiration, Photosynthesis, and Water-Use Efficiency", *Water Resources Res.*'6:280-289.
Adegoroye et al.; 1983; "Initiation and Control of Sunscald Injury of Tomato Fruit Lycopersicon Esculentum, Solar Injury, Radiation Stress"; *J. Am. Soc. Hortic. Sci.*; 108:23-28.
Applications Support Glossary; *The PQ Corporation*; as early as Jun. 17, 2003; pp. 1-20; http:///www.pqcorp.com/technicalservice/glossary.asp.
Amdt; 1992; "Apple Shading to Reduce Heat Damage"; *Tree Fruit Leader V1, Govt of British Columbia, Ministry of Agriculture, Food and Fisheries*; http://www.agf.gov.bc.ca/treefrt/newslett/appleshading.htm.
Basnizki et al.; 1975; The Influence of a Reflectant on Leaf Temperature and Development of the Globe Artichoke (Cynara Scolymus L.); *J. Amer. Soc. Hort. Sci.*; 100:109-112.
Drake et al.; 1991; "Quality and Storage of 'Granny Smith' and 'Greenspur' Apples on Seedlings, M. 26 and MM.111 Rootsocks"; *J. Am. Soc. Hortic. Sci.*; 116:261.264.
Glenn et al.; 2002; "A Reflective, Processed-Kaolin Particle Film Affects fruit Temperature, Radiation Reflection and Solar Injury in Apple"; *J. Am. Soc. Hortic. Sci.*; 127:188-193.
Glenn et al; 1999; "Hydrophobic Particle Films: A New Paradigm for Suppression of Arthropod Pests and Plant Disease"; *J. Econ. Entom.*; 92:759-771.
Glenn et al., 2001; "Particle Film Application Influences Apple Leaf Physiology, Fruit Yield, and Fruit Quality"; *J. Am. Soc. Hort. Sci.*; 126:175-181.
"Guar Gum"; as early as Jun. 17, 2003; pp. 1-2; http://www.sbu.ac.uk/water/hygua.html.
Harper et al.; "Cleaning Compounds: Characteristics and Functions"; *Department of Food Science and Technology, Ohio State University*; as early as Jun. 17, 2003; pp. 1-11; http://216.239,51.100/search?q=cache:d9pZuBLHWJAJ:class.fst.ohio-state.edu/fst401/Infor....
Khemira et al.; 1993; "Hedgerow Orientation Affects Canopy Exposure, Flowering, and Fruiting of 'Anjou' Pear Trees"; *HortScience*; 28:984-987.
Knight et al.; 2001; "Impacts of seasonal Kaolin Particle Films on Apple Pest Management"; *Can. Entomol.*; 133:413-428.
Liang et al.; 2002; "Repellency of a Kaolin Particle Film, Surround, and a Mineral Oil, Sunspray Oil, to Silverleaf Whitefly (Homoptera:Aleyrodidae) on Melon in the Laboratory"; *J. Econ. Entomol.*; 95:317-324.
Lipton; 1977; "Ultraviolet Radiation as a Factor in Solar Injury and Vein Tract Browning of Cantaloupes"; *J. Am. Soc. Hortic. Sci.*; 102:32-36.
"Locust Bean Gum"; as early as Jun. 17, 2003; pp. 1-2; http://www.sbu.ac.uk/water/hyloc.html.

(Continued)

*Primary Examiner*—Johann R. Richter
*Assistant Examiner*—Ali Soroush
(74) *Attorney, Agent, or Firm*—Sheridan Ross P.C.

(57) ABSTRACT

This invention relates generally to crop protection compositions and methods for making and using the compositions. More specifically, the invention relates to crop protection compositions utilizing talc and one or more additives providing for improved aqueous suspension of the talc and methods for making such compositions. The present invention also discloses horticultural substrates coated with a crop protective composition utilizing talc and one or more additives providing for improved aqueous suspension of the talc.

19 Claims, No Drawings

OTHER PUBLICATIONS

Mitchum; "Fruit Physiological Disorders: Apple Sunburn (Sunscald"; *Postharvest Technology Research and Information Center, University of California at Davis*; 1996-2004; pp. 1-2; http://postharvest.ucdavis.edu/produce/disorders/apple/pdapsun.shtml.

Parchomchuk et al.; 1996; "Orchard Cooling With Pulsed Overtree Irrigation to Prevent Solar Injury and Improve Fruit Quality of 'Jonagold' Apples"; *HortScience*; 31:802-804.

Puterka et al.; 2000; "Progress Toward Liquid Formulations of Particle Films for Insect and Disease Control in Pear"; *Environ. Entomol*; 29:329-339.

Roberts et al.; 1994; "Canopy Shade and Soil Mulch Affect Yield and Solar Injury of Bell Pepper"; *HortScience*; 29:258-260.

Schrader et al.; "Raynox for Suppression of Pests in Apple and Pear"; *Washington State University Cooperative Extension Service*; (date unknown); http://www.tfrec.wsu.edu/staff/les.htm; 1 p.

Schrader et al.; "Stress-Induced Disorders: Effects on Apple Fruit Quality"; *Washington Tree Fruit Postharvest Conference*; Dec. 2-3, 2003; pp. 1-7.

Schupp et al.; 2002; "Effect of Particle Film on Fruit Sunburn, Maturity and Quality of 'Fuji' and 'Honeycrisp' Apples"; *Hort. Technology*; 12:87-90.

"Slip Information from Dalzell Crafts and Ceramics, Your Source for Bisque"; *DCC*; as early as Jun. 17, 2003; pp. 1-2; http://216.239.51.100/search?q=cache:2xomX3xEnvUJ:www.dalzell.net/ceramics/slip.html+....

Sparks; 1995; "Environmental Soil Chemistry: Chapter 2: Inorganic Soil Components"; *Academic Press*, San Diego; p. 36.

Spayd et al.; "Separation of Sunlight and Temperature Effects on the Composition of *Vitis vinifera* cv. Merlot Berries"; *Am. J. Enol. Vitic.*; 2002, 53:3; pp. 171-182.

Stemmermann et al.; 1978; "Talc-Coated Rice as a Risk Factor for Stomach Cancer"; *Am. J. Clin. Nutr.*;31:2017-2019.

Stern; "Particle Film Enters the Picture: Whitewash-like Spray Repels Pome Fruit Pests, Helping Cut Pest-Control Costs"; *The Grower*;(date unknown; pp. 1-3; http://www.growermagazine.com/home/04-02surround.html.

"Surround WP Crop Protectant—Specimen Label"; *Engelhard*; as early as Mar. 26, 2001); 9 pp.

"Surround Crop Protectant"; *Surround WP Manufacturer; Engelhard Corporation*, 101 Wood Avenue, P.O. Box 770, Iselin, NJ 08830-0770; 2pp.; http://www.surround.engelhard.com.

"Talc Mineral Data Pronunciation Guide"; *Trinity Mineral Co.—Rare Minerals*; Apr. 20, 2003; pp. 1-3; http://webmineral.com/data/Talc.shtml.

"Understanding Plainsman Data Sheets"; *Plainsman Clays Ltd.*; as early as Jun. 10, 2003; pp. 1-6; http://digitalfire.com/plainsman/overview.shtml.

Unruh et al.; 2000; "Particle Films for Suppression of the Codling Moth (Lepidoptera:Torticidae) in Apple and Pear Orchards"; *J. Econ. Entomol.*; 93:737-743.

"Virta; United Staes Geological Survey"; 2002; Minerals Yearbook.
Warmund; "Top Crops"; *University of Missouri, in cooperation with the Missouri State Horticulture Society*; Summer 2004; pp. 1-6; http://www.agebb.missouri.edu/hort/topcrops.htm.

* cited by examiner

COMPOSITION AND METHOD FOR CROP PROTECTION

CROSS-REFERENCE TO RELATED APPLICATION

This application claims priority under 35 U.S.C. § 119(e) from U.S. Provisional Application Ser. No. 60/499,055, filed Aug. 29, 2003, which is incorporated herein by reference in its entirety.

FIELD OF THE INVENTION

This invention relates generally to crop protection compositions and methods for making and using the compositions. More specifically, the invention relates to crop protection compositions utilizing talc and one or more additives providing for improved aqueous suspension of the talc and methods for making such compositions. The present invention also discloses horticultural substrates coated with a crop protective composition utilizing talc and one or more additives providing for improved aqueous suspension of the talc.

BACKGROUND OF THE INVENTION

Plants on land areas experience extreme environmental conditions, such as variations in air temperature, wind speed, light levels, relative humidity and available nutrients and water. Increasing foliage reflectance is recognized as a means of moderating environmental conditions leading to such conditions as heat stress and sunburn on plants. Reflective coatings may be applied to the surfaces of fruits and vegetables to reduce excessive heat and light (including ultraviolet and infrared light) at the fruit/vegetable surface in an attempt to prevent "sunburn." Sunburn appears as a darkened area on the surface of fruits and vegetables. Beneath the sunburned area, the fruit/vegetable tissue is damaged and likely to develop disease symptoms. The strategy of applying a reflective treatment is to reduce the temperature of the fruit by reflecting heat or by blocking light.

However, many of the methods known in the art to increase reflectance of foliage cause decreased transpiration and decreased photosynthesis. Photosynthesis and transpiration are necessary for the plant to grow and/or produce a useful crop. Other methods for reducing environment stress on plants are described in U.S. Pat. No. 6,069,112, 6,156,327, 6,027,740 and 5,908,708. These patents describe and include methods and compositions comprising heat treated particulate materials including heat treated kaolin.

Talc is a naturally hydrophobic mineral and resists wetting by water. The hydrophobicity of talc would be an advantage for reflective compositions for plants. Once present as a film on a plant surface, talc is predicted to resist removal by water, present in the form of rain, irrigation, humidity and the like. Thus, a reflective layer of talc on a surface of a plant would be predicted to be more long lasting than a similar hydrophilic reflective layer. Thus, it is desirable to form a talc layer on plant surfaces. However, wetting talc with water to create a slurry for application to plants can be difficult. Talc placed in water exhibits a slow makedown, i.e. delayed suspension upon addition of water to form a slurry, and also exhibits clearing, i.e. settling of a slurry into a sediment resulting in a supernatant fluid layer that has been cleared of talc thus appearing clear to the eye. These properties can be troublesome to a user attempting to create a slurry of talc in water in that creating a slurry is more time-consuming, and the slurry needs more agitation in order to be effective. Another problem for the user is the problem of a "hard heel" or the development of a sediment that resists resuspension. Such a hard heel is also disadvantageous because the hard heel may be difficult to remove from spraying equipment and may clog lines.

Accordingly, there remains a need in the art for methods and compositions that protect plants and crops from environmental stresses such as sunburn while enhancing the ease of application for the user. For example, conventional treatments for protecting crop plants include the use of reflectant particles which are supplied as a powder to the user. Generally, application of a powder to the plant is not commercially practical on a large scale due to drift and inhalation hazards. Instead, the product must be applied as a slurry. However, the user may experience inconvenience and hazards associated with handling a powder during the process of preparing a slurry. Powders are messy. Powders can easily spill and are difficult to completely remove. They may aerosolize and enter the air, causing an inhalation hazard to the worker and to any others nearby. There also remains a need in the art for crop protectant compositions and methods that minimize or prevent user's exposure to dusts and powders, yet retain their ability to go into an aqueous suspension or "slurry." There also remains a need in the art for crop protectant compositions and methods that readily wet plant surfaces and that can be removed by simple washing.

There also remains a need in the art for crop protectant compositions and methods that utilize materials that are "natural" or organic, i.e. compositions and methods that are compatible with the production and handling of organic crops and organic processed food products, as defined by the United States Department of Agriculture under the 1990 Organic Foods Production Act.

SUMMARY OF THE INVENTION

In one embodiment, the present invention includes a slurry composition for protecting crops. The composition includes a phyllosilicate mineral, a chelating agent, and multivalent ions. Further, the composition has a pH of between about 9.0 and about 11.6. The phyllosilicate material can be selected from kaolinites, talcs, chlorites, pyrophyllites, montmorillonites, smectites and vermiculites, and in a preferred embodiment, is talc. The chelating agent can be selected from sodium maleate, citric acid, sodium citrate, sodium aluminate, sodium silicate, EDTA, DTPA, and mixtures thereof, and in a preferred embodiment, is citric acid. The multivalent ions can comprise cations selected from magnesium ions and aluminum ions. The multivalent ions can also include anions selected from sulfate ions and citrate ions. In a preferred embodiment, the multivalent ions are from magnesium sulfate heptahydrate.

In a further embodiment of the present invention, a composition that is useful for producing a slurry for protecting crops is provided. The composition includes a phyllosilicate material, a chelating agent and a source of multivalent ions for when the composition is used in the production of a slurry. In a preferred embodiment, the chelating agent is citric acid and the multivalent ions are magnesium and sulfate ions from Epsom salt. In this embodiment, the citric acid and Epsom salt are present in a ratio of between about 1:0.5 to about 1:10 citric acid:Epsom salt.

A further embodiment of the present invention is a method for crop protection that includes applying to at least a portion of a surface of a crop an effective amount of a slurry composition as described herein. The step of applying can be performed by spraying, painting and dipping. The crop can be selected from fruits, vegetables, grains, legumes, trees, shrubs, flowers, grasses, roots, landscape plants, ornamental plants, and crop plants.

A further embodiment of the present invention is a method for protecting crops from freezing that includes applying to at least a portion of a surface of a crop an effective amount of a slurry composition as described herein. The method can be conducted in combination with other known techniques for preventing freezing of crops such as covering plants and burning smudge pots.

A further embodiment of the present invention is method for protecting crops from pest infestation that includes applying to at least a portion of a surface of a crop an effective amount of a slurry composition as described herein.

A further embodiment of the present invention is a coated substrate that is a horticultural substrate wherein at least a portion of the surface of the substrate is coated with a crop protectant composition. The composition comprises the residue of a slurry composition as described herein.

A further embodiment of the present invention is a composition for application to crops that includes talc, citric acid, magnesium sulfate heptahydrate, and soda ash. The talc can be present in an amount between about 75 dry wt. % to about 99 dry wt. %; the citric acid can be present in an amount between about 500 ppm and about 2000 ppm; the magnesium sulfate heptahydrate can be present in an amount between about 1000 ppm and about 4000 ppm; and the soda ash can be present in an amount between about 1 dry wt. % and about 4 dry wt. %. In a preferred embodiment, the talc is present in an amount of about 97.125 dry wt. %, the citric acid is present in an amount of about 0.125 dry wt. %, the magnesium sulfate heptahydrate is present in an amount of about 0.25 dry wt. %, and the soda ash is present in an amount of about 2.5 dry wt. %. This composition can be in pellet form or can be a slurry further comprising water. In the embodiment of a slurry, the composition can have a pH of between about 9.0 and about 11.6.

DETAILED DESCRIPTION OF THE INVENTION

The present invention comprises a crop-protective composition and process and a treated substrate. The composition of the invention has the ability to wet and coat fruits and other crops well for protection from sunburn, for example. The composition can be applied to a wide range of fruit, vegetable or other crop surfaces by a variety of application methods. The components of the composition can be mixed and dispersed, for example, in pellet form so that an end-user, such as a farmer, can simply mix the pellets with water and achieve the correct pH and chemical composition. The composition can be formulated with environmentally acceptable components while still meeting significant surface chemistry requirements. In slurry form, the composition can be a stable suspension to allow for application to crops and avoiding plugging of equipment with solids. The description which follows describes a preferred embodiment of the invention, and various alternative embodiments. It should be readily apparent to those skilled in the art, however, that various other alternative embodiments may be accomplished without departing from the spirit or scope of the invention.

One embodiment of the present invention is a composition for protecting crops. The word "crops" can refer to any type of plant or product of a plant, such as fruits, vegetables, grains, legumes, trees, shrubs, flowers, grasses, roots, landscape plants, ornamental plants, and crop plants. Protecting crops refers the ability of a compound of the present invention to prevent and/or reduce and/or minimize undesirable effects of sun and/or heat. Undesirable effects of sun and/or heat on crops includes sunburn and heat stress, all of which may increase transpiration during photosynthesis, or cause visual damage to plant products such as fruits, vegetables, and fibers. Protecting crops also refers to the ability of a compound of the present invention to prevent and/or reduce and/or minimize insect infestation and/or damage to plant products.

According to the invention, the composition for protecting crops includes a phyllosilicate mineral, a preferred embodiment of which is talc, a hydrous magnesium silicate. The composition of the present invention also includes a chelating agent and multivalent ions.

The term "phyllosilicate mineral" (phyllosilicate) refers to those minerals that contain basic silicates. Preferably the phyllosilicate is selected from the group consisting of kaolinites, talcs, chlorites, pyrophyllites, montmorillonites, smectites and vermiculites. More preferably, the phyllosilicate is selected from the group consisting of talcs and pyrophyllites, and most preferably the phyllosilicate is talc.

Talc, in its unadulterated form, is a platy mineral, meaning that talc will crystallize in a thin sheet and will tend to flake along cleavage planes. Talc can be processed for use in the present invention by any suitable method, such as dry milling. The talc particles may be screened to the desired median particle size. Another talc milling method is a fluidized energy method ("FEM"). Here, the talc is mixed into a slurry with water (steam) such that the talc is held in suspension and the talc particles are ground and/or sorted to achieve the right particle size distribution curve. Talc is a naturally hydrophobic mineral and resists wetting by water. The compositions of the present invention typically contain a phyllosilicate mineral in amount from about 50 dry wt. % to about 99.9 dry wt. % (i.e., based on dry weight of material used to make a slurry). More preferably, compositions of the present invention contain phyllosilicate mineral present in an amount from about 75 dry wt. % to about 99 dry wt. %, from about 90 dry wt. % to about 98 dry wt. %, and from about 95 dry wt. % to about 98 dry wt. %. In a preferred embodiment, phyllosilicate mineral is contained in an amount of about 97 dry wt. %. In a particularly preferred embodiment, the phyllosilicate mineral is talc and is present at 97.125 dry wt. %. In this embodiment, the composition can also include about 2.5 dry wt. % soda ash, about 0.125 dry wt. % citric acid, and about 0.25 dry wt. % Epsom salt and can be in pellet form. The multivalent ions of the present compositions can be provided by salts that possess both multivalent cations such as magnesium (+2) and aluminum (+3) and multivalent anions such as sulfate (−2) and citrate (−3). More preferably, multivalent anions useful in the present invention can be selected from the group consisting of magnesium (+2), aluminum (+3), among others. Multivalent cations useful in the present invention can be selected from the group consisting of sulfate (−2) and citrate (−3), among others. In a preferred embodiment, the multivalent ions are from Epsom salt (magnesium sulfate heptahydrate) which is typically present in the slurry composition at a concentration of between about 1000 ppm and about 4000 ppm, between about 1500 ppm and about 3500 ppm, between about 2000 ppm and about 3000 ppm, and preferably about 2500. As used in this invention, parts per million (ppm) values are reported on by weight of dry solids basis, i.e., not including water or any other solvent, unless noted otherwise.

The chelating agents of the present invention are molecules with monovalent anionic sites on a multivalent backbone. The preferred chelating agents are sodium maleate, citric acid, sodium citrate, sodium aluminate, sodium silicate, EDTA, DTPA and combinations of these agents. Most preferably, the chelating agent is citric acid. The multivalent cations can react with the polymeric anionic strings (chelation) but with some difficulty due to the attempt to capture several anionic sites to reach electrostatic neutrality. Thus, the chelating agent operates by wrapping around a multivalent cation, the phyllosilicate particle in suspension. In the embodiment in which the chelating agent is citric acid, the citric acid is typically present in the slurry composition at a concentration of between about 500 ppm and about 2000 ppm, between about 750 ppm and about 1750 ppm, between about 1000 ppm and about 1500 ppm, and preferably at about 1250 ppm.

In the embodiment in which the multivalent ions are provided by Epsom salt and the chelating agent is citric acid, the citric acid and the Epsom salt are preferably present in a ratio of between about 1:0.5 to about 1:10 citric acid:Epsom salt, more preferably about 1:1 to about 1:7, more preferably about 1:1.5 to about 1:4, and most preferably about 1:1.85 to about 1:2.

The present invention provides means of forming crop protective mineral slurries that are highly stable during transport and storage. Using chelating agents, multivalent ions, and pH control, the present invention provides a crop protective mineral slurry that is stabilized to prevent sedimentation.

As used in the present disclosure, the term "stability" specifically means that the individual mineral particles in the slurry of the present invention refrain from coagulation or flocculation in suspension or coalescence on the bottom of the container. Stability comes from having a very uniform electrostatic charged field around each particle in the suspension. The electrostatic particle-to-particle repulsion will exceed gravity forces that seek to drive sedimentation of the suspension. For practical purposes of the present disclosure, a suspension is considered to be stable if the coagulation process is so slow as to take at least five, ten or fifteen days to form a perceptible precipitate in an undisturbed shipping container.

Slurry compositions of the present invention have improved rheological properties and low viscosity. "Improved rheological properties" and "a low viscosity" means that the flow characteristics of the slurry of the present invention are improved over the flow characteristics of a conventional talc slurry when the two slurries are compared at equivalent solids content and that the slurry of the present invention can be worked and/or pumped by means which are conventional, depending on the desired use of the slurry. The slurry of the present invention has a rheology which permits, among other things, ease of transfer and use. Preferably the viscosity of the slurry is less than about 500 centipose (cps), more preferably less than about 350 cps, and most preferably less than about 200 cps.

The term "high solids" refers to those slurries in which the content of phyllosilicate mineral is at least about 45% by weight, at least about 50% by weight, at least about 55% by weight, and preferably is between about 45% by weight and about 55% by weight.

The Schulze-Hardy rule for flocculation of sols states that the flocculating value of an electrolyte is predominantly determined by its valence rather than its type. Consequently, divalent and trivalent cations or anions are significantly more powerful in flocculating a sol than monovalent ions in solution. The stabilizing technology of the present invention uses multivalent cations and anions as antagonists to the dispersing action of special chelating or dispersing agents. The best rheology of the final slurries of the present invention is obtained by following specific process steps, but the stabilizing results are not dependent on these steps.

One embodiment of the present invention provides a process of making a high content, stable mineral slurry. Without being bound by theory, it is believed the process is conducted by attaching the multivalent chelating agent onto the edge of the mineral. The process includes first adding the chelating agent to the suspension in which the mineral is dispersed in a high pH aqueous environment. The crystal structure of phyllosilicate minerals is such that there is a net negative electrostatic charge on the faces and a net positive charge on the edges of the crystal. The chelating agent is believed to attach to the edges of the mineral crystals, as there are magnesium cations in the crystal lattice as brucite. The chelating agents cannot remove the magnesium, and therefore become electrostatically bound to the mineral.

The pH of the slurry is from about pH 9.0 to about pH 11.6, more preferably from about pH 9.5 to about pH 10.5, more preferably from about pH 9.7 to about pH 10.3 and most preferably about pH 10. The pH of the slurry can be adjusted after the slurry has formed, continuously throughout the makedown process, during each addition of phyllosilicate mineral, or at any time during the makedown process. Preferably, the pH of the slurry is maintained at a desired level throughout the makedown process. This can be achieved by continuously monitoring the pH of slurry and adjusting the pH as needed. The monitoring and addition of a pH control agent can be done manually or it can be done automatically, e.g., by a computer controlled process. In a preferred embodiment, pH is controlled by the inclusion of sodium carbonate (soda ash) in compositions of the present invention. The amount of sodium carbonate or other pH control agent is such that the pH parameters described above are achieved. In the embodiment in which soda ash is the pH control agent, it is typically present, on a dry weight basis, such as in a pellet, at a level of between about 1 dry wt. % and about 4 dry wt. %, between about 1.5 dry wt. % and about 3.5 dry wt. %, between about 2 dry wt. % and about 4 dry wt. %, and preferably, about 2.5 dry wt. %.

An excess of multivalent cations such as aluminum or magnesium is then added. The chelating agent attempts to wrap around these cations as well but is unable to as it is already attached to the mineral surface in a linear arrangement. Typically, magnesium or aluminum cations cause a rheology crisis within a mineral slurry manifested by rheopectic behavior if the pH range is outside the limits set here. However, without intending to be bound by any one theory, when used in the methodology of the present invention, divalent anions such as sulfate, phosphate and tetraborate, appear to act as anionic dispersants maintaining low viscosity during gentle or severe agitation. The methodology of the preferred embodiments of the present invention do not induce any rheopectic or dilatent behavior in the mineral slurry. Thus, the addition of salts composed of multivalent cations and anions to the mineral slurry containing chelating agents creates an ionic environment leading to a slurry having long-term stability.

The makedown process of the present invention can include adding a feedstream of phyllosilicate to the aqueous composition at a rate and under conditions sufficient to obtain a substantially homogeneous high solids slurry. Preferably, the mass median $d_{50}$ of the phyllosilicate is less than about 7 micron (μm), more preferably from about 1.2 μm to about 3.5 μm. A "mass median $d_{50}$" refers to a particle size distribution wherein about 50% of total weight of phyllosilicate is due to particles having less than the mass median $d_{50}$ particle size. Alternatively, it is preferred that the particle size of about 100% of phyllosilicate is less than about 44 μm.

Alternatively, instead of comminuting the phyllosilicate to a desired particle size prior to the makedown process, a high solids content slurry makedown process of the present invention may be conducted prior to a comminuting process. For example, a high solids content slurry having a relatively large phyllosilicate particle size can be subjected to a wet-milling process to produce a slurry having a desired phyllosilicate particle size. In this manner, the milling process also provides the shearing action required for the makedown process. Moreover, this wet-milling eliminates a need for a separate entrained air removal step.

It has been observed that the ease of preparation of a high solids content low viscosity slurry is dependent on the temperature of the slurry during the makedown process. Preferably and surprisingly, it has been found conducting the makedown process at lower temperatures results in improved rheology and reduced viscosity. In particular, preferably, the makedown process is conducted at temperatures from about 5° C. to about 20° C., from about 6° C. to about 16° C., and preferably, from about 7° C. to about 12° C. It should be appreciated that the above temperature refers to a temperature during a makedown process only; thus, after the makedown process, the temperature of slurry can be outside of these temperatures.

The makedown process can be facilitated by high shear agitation of the aqueous composition as the feedstream of than about 500 cps once flowing. This reversible plastic behavior in conjunction with the electrostatic sol stabilization is thought to be the cause for the exceptional functional slurry stability of the slurries of the present invention.

The stoichiometry of the reaction guides the formation of the optimal stabilizing formulation. For example:

| 2 HO—C—COOH + —COOH —COOH Citric acid | 3 $MgSO_4.7H_2O$ + Epsom salt | 6 NaOH Base | ® $Mg_3Cit_2$ Magnesium Citrate | +3 $Na_2SO_4$ Sodium sulfate |
|---|---|---|---|---|
| MW = 192.2 * 2 384 1250 PPM | 246.3 * 3 738 2500 PPM (stoichiometric ratio of salt and chelating agent) | 40.6 * 6 240 | 355 1155 | 426 1390 | phyllosilicate is added to a mixing tank. Preferably, the tip speed of the mixer blade in the mixing tank is from about 4000 feet per minute (fpm) to about 9000 fpm. If the feedstream is added too quickly, the slurry rheology becomes too stiff and difficult to stir. In such a case, the slurry can be allowed to stand without mixing and the stirring can be started when the viscosity of slurry decreases due to peptization via diffusion of electrolytes. In order to avoid having to wait for peptization by diffusion, preferably the feedstream is added at a rate of from about 300 grams/minute per liter of aqueous composition (g/min/l) decreasing to about 60 g/min/l until the slurry reaches about 55% solids. As will be appreciated, as the amount of solids increase in the slurry the feedstream must be added at a slower rate to allow complete peptization to occur and to allow entrained air to escape. Thus, when the solids content reaches about 55%, the addition of feedstream is further decreased to about 40 g/min/l until a desired solids content is reached.

The presence of air in the slurry affects the viscosity of the slurry. It is believed that the primary source of air is from the agglomerated phyllosilicate particles. The agglomerated phyllosilicate particles can be 40% air with phyllosilicate particles being held together by van der Waals force. During the makedown process, air is released from the phyllosilicate particle surface in the slurry but is held in the slurry suspension. Preferably the slurry contains less than about 3.5% by volume of entrained air, more preferably less than about 2%, and most preferably less than about 1%.

One can reduce the amount of entrained air in the slurry by allowing the air to escape from the slurry during the makedown process. This provides a slurry with a reduced viscosity. The removal of entrained air can be accomplished by stopping the high shear agitation for a time sufficient to allow the entrained air to escape or by transferring the slurry to a holding tank. When using a single tank system, the slurry is typically allowed to rest for an average time of from about 10 min. to about 40 min. The slurry is then resubjected to mixing to further increase the solids content.

The slurries of the present invention have the normal pseudoplastic rheology in an agitated state that is expected from these mineral slurries. This behavior is consistent over a wide range of temperature from freezing to values as high as 150° F. and above. On standing for as little as about four hours, the slurry develops a gelled characteristic. The fluid form is described as a "Bingham plastic." A degree of fluid shear must be imparted to start the fluid moving again. Viscometer tests indicate low speed viscosities of as much as about 40,000 cps on a standing gel that breaks down to less It has been discovered empirically that significant reductions in the amounts of citric acid or EDTA generate better stability than precise stoichiometric ratios of these two chelating agents.

Although many different solvents can be used in making slurries of the present invention, the preferred solvent is water. Upon the introduction to hard water, chelating agents encounter metal cations ($Mg^{++}$ and $Ca^{++}$). The quantities of the chelating agents used in these mineral slurries are lower than stoichiometric amounts given the content of divalent cations in the hard water. For this reason, the methods of producing the mineral slurries of the present invention include the makedown at elevated pH before the chelating agent is introduced. The elevated pH causes precipitation of cations found in hard water. The chelating agents then have a much higher probability of attachment to the cationic sites at the edge of the mineral rather than sequestering minerals in hard water.

The presence of carbonate minerals in talc products such as dolomite or magnesite will influence the ratio of stabilizing chemicals. An examination conducted to test for reduced sedimentation rates in slurries of the present invention formed with talc and citric acid and Epsom salt resulted in the exemplary ratios shown in Table I.

TABLE I

| Talc source | Production Process | Citric acid | Epsom salt | Ratio (chelating agent to salt) |
|---|---|---|---|---|
| Yellowstone, Montana | Reduced surface energy | 1250 PPM | 2500 PPM | 1:2 |
| Yellowstone, Montana | Reduced surface energy | 1400 PPM | 2600 PPM | 1:1.9 |

These ratios in Table I are not necessarily at the limits of the best performance but do provide a functional stability. Although, slurries may have increasing stability with higher concentrations of salts, the best balance for different mineral slurries is often based not only on stability but on a combination of stability, cost and rheology considerations.

In alternative embodiments, the composition of the present invention can also include an oil. Such oils can include vegetable oils, such as soybean oil, corn oil, and canola oil, which can be composed of triglycerides of oleic and linoleic acids. In such embodiments, the oil can be present in amounts from about 0.1% to about 10% by weight of a slurry composition, from about 0.5% to about 5% by weight of a slurry composition, from about 0.75% to about 2% by weight of a slurry composition, and most preferably, about 1% by weight. It has been found that the inclusion of oils can improve the stability of the phyllosilicate material suspension in the slurry. In addition, such oils may have additional benefits, such as, for example, controlling pests. For example, soybean oil has been used as a dormant spray and a summer spray for the control of pear psylla. Psylla are any of various jumping plant lice of the family Psyllidae, especially of the genus Psylla, several species of which infest fruit trees.

In one embodiment, the composition of the present invention is in the form of a powder. In a more preferred embodiment, the composition of the present invention is formed into a pellet. Pelleting can be accomplished by methods known in the art and include all such methods. Pellets are advantageous in that they represent a form that is more convenient for use than bulk powders. Pellets are more flowable and easier to handle and use. For example, they are more easily cleaned up when spilled than powders. Another advantage of a pellet is a significant reduction of user's dust exposure with pellets formulations compared to bulk powders. Pellets may be weighed, transferred and otherwise handled with a significant reduction in generated dust compared to powders. Pellets of the present invention may be of any size and shape convenient for use.

In one embodiment of using the present invention, the powders or pellets are combined with water to form a slurry for ease of application to crops. Preferably, a slurry of the present invention is formed by combining the powder or pellets with water and agitating the mixture with an agitator. The solid content of a slurry of the present invention can be any suitable solids content for achieving desired crop protection and in particular, may range from about 5% to about 55%. Optionally, occasional stirring may be used to help keep the slurry dispersed.

Compositions of the present invention can be formulated in any manner conventional in the art. In a preferred embodiment, the chelating agent (e.g., citric acid) and a source of multivalent ions (e.g., Epsom salts), along with other components such as soda ash for pH control can be formed into a pellet of the phyllosilicate material. For example, in the instance of talc, pellets are prepared by mixing talc and water, forming the pellet, and drying the pellet to a residual moisture content of about 2-3%. In such a process, citric acid and Epsom salts can be premixed with soda ash being blended into the premix, and then adding the blend to water. Such a solution is then mixed with talc and pellets formed as described above. In this manner, intimate mixing of the phyllosilicate material with other components is achieved. Additionally, undesirable interactions can be reduced or avoided by mixing the Epsom salt with the citric acid before addition of the soda ash. Otherwise, the soda ash and citric acid can react and effervesce. Alternatively, pellets of the phyllosilicate material can be formed with only water and additional components added when a slurry is formed. Also, in embodiments in which the phyllosilicate material is not pelleted, any additional components can be blended dry as loose powders before preparation of a slurry or simply added to water and the phyllosilicate material at the time the slurry is formed.

Another embodiment of the present invention includes a method for crop protection, comprising applying to at least a portion of a surface of a crop an effective amount of a composition of the present invention. Application may be made by any process known in the art. One method of applying a composition of the present invention is by dusting. A more preferred method of applying a composition of the present invention is to first, form a slurry of the present invention and then apply the slurry to the surface of the crops. Methods to apply slurries are known in the art, and include spraying, painting, and dipping. A preferred method to apply a slurry of the present invention is to spray. To obtain an effective amount of the composition of the present invention on the surface of a plant, at least one application is required. In preferred embodiments, during the course of a growing season, the composition can be applied 2, 3, 4 times or more.

A further embodiment of the present invention is a method for protecting crops from freezing. Application of compositions of the present invention to crops protects crops from being damaged from freezing due to low ambient temperatures or lowers the temperature at which damage occurs. Compositions of the present invention can be applied to crops in locations that are at risk of damage due to low temperatures, such as crops early in the spring season when temperatures can go near or below freezing or crops that are grown in colder climates. Application of compositions of the present invention for preventing freeze damage can be used alone or in conjunction with other known techniques such as covering plants or burning smudge pots.

A further embodiment of the present invention is a method for controlling pests. Application of compositions of the present invention to crops protects crops from infestation or the spread of infestation of pests, such as aphids. Compositions of the present invention can be applied to crops in locations that are at risk of damage due to pests. Application of compositions of the present invention for controlling pests can be used alone or in conjunction with other known techniques of pest control.

In another embodiment, the present invention relates to a substrate coated with a composition comprising a residue of a slurry composition of the present invention. Reference to a residue includes the composition as it initially lands on a substrate and well as subsequent stages of drying and/or subsequent rehydration (e.g., from ambient precipitation). The substrate includes a horticultural substrate. Suitable horticultural substrates include fruits, vegetables, grains, legumes, trees, shrubs, flowers, grasses, roots, landscape plants, ornamental plants, and crop plants. The surface of the substrate is coated with a composition of the present invention. Methods for coating the surface of the substrate include application to the surface via methods of application suitable for the present invention, and allowing the surface to dry.

EXAMPLES

Example 1

This Example describes the wet-out and dispersion characteristics of talc formulations of the present invention. The additives tested are soda ash and Epsom salts.

To determine the makedown and dispersion characteristics of each talc formulation, the following procedures were used. Dry powdered talc was formulated with the addition of the additives Epsom salt and/or soda ash. The formulations were then formulated into pellets. 25 gram (g) pellets were added to 1 liter (L) beakers and 500 milliliter (mL) water was added. Suspensions were then dispersed in a Waring blender and filtered through a 325 mesh screen. At this time, makedown rate (ability to go into suspension) was assessed and was rated as follows: "fast" makedown refers to talc that went into suspension within 5 minutes; "slow" makedown refers to talc that went into suspension between 5 minutes and 30 minutes. Suspensions were then placed back into a 1 L beaker and allowed to rest for a period of time, generally one hour. At the end of the resting time, suspensions were rated on their settling rate. "Fast" settling rates refers to suspensions where the talc had settled out by the end of the resting time. Suspensions which were settling at a "slow" rate were assessed for whether the suspended talc was curdled or flocculated. Table 1 describes the results of this Example.

TABLE 1

Talc formulations and makedown rate, settling rate, and suspension characteristics

| Formulation, name | wt. % soda ash | wt. % Epsom salt | pH | settling time | makedown rate | settling rate | curdled or flocculated? |
|---|---|---|---|---|---|---|---|
| Control | 0 | 0 | 8.5 | 1 hour | fast | fast | no |
| soda ash | 0.5 | 0 | 9.5 | 1 hour | fast | fast | no |
| soda ash | 1 | 0 | 9.9 | 1 hour | fast | fast | no |
| epsom salt | 0 | 1 | 8.5 | 1 hour | fast | fast | no |
| epsom salt | 0 | 2 | 8.4 | 1 hour | fast | fast | no |
| soda ash/epsom salt | 1 | 2 | 9.5 | 1 hour | fast | fast | no |
| soda ash/epsom salt | 0.5 | 1 | 9.3 | 1 hour | fast | fast | no |
| soda ash/epsom salt | 0.5 | 2 | 9.3 | 1 hour | fast | fast | no |
| soda ash/epsom salt | 1 | 1 | 9.7 | 1 hour | fast | fast | no |

Table 1 shows the results of talc formulations with soda ash, epsom salts, or both. All the formulations tested in this Example had a relatively quick makedown, but failed to stay in suspension during the resting phase of the experiment.

Example 2

This Example describes the wet-out and dispersion characteristics of talc formulations of the present invention. The additives tested are borax and epsom salts.

Experiments to determine makedown, settling, and curdling/flocculation were performed as described in Example 1. Talc formulations were prepared as described in Example 1. In this Example, additives tested were Epsom salt and/or borax.

TABLE 2

Talc formulation and makedown rate, settling rate, and suspension characteristics

| Formulation name | wt. % borax | wt. % Epsom salt | pH | settling time | makedown rate | settling rate | curdled or flocculated? |
|---|---|---|---|---|---|---|---|
| control | 0 | 0 | 8.5 | 1 hour | fast | fast | none |
| borax/epsom salt | 1 | 1 | 8.9 | 1 hour | fast | fast | none |

Table 2 shows the results of talc formulation with soda ash and epsom salts. The formulation had a relatively quick makedown, but failed to stay in suspension during the resting phase of the experiment.

Example 3

This Example describes the wet-out and dispersion characteristics of talc formulations of the present invention. The additives tested are citric acid and epsom salts.

Experiments to determine makedown, settling, and curdling/flocculation were performed as described in Example 1. Talc formulations were prepared as described in Example 1. In this Example, additives tested were Epsom salt and/or citric acid.

TABLE 3

Talc formulations and makedown rate, settling rate, and suspension characteristics

| Formulation, name | wt. % citric acid | wt. % Epsom salt | pH | settling time | makedown rate | settling rate | curdled or flocculated? |
|---|---|---|---|---|---|---|---|
| control | 0 | 0 | 8.5 | 1 hour | fast | fast | none |
| citric acid | 0.1 | 0 | 7.9 | 1 hour | fast | fast | none |
| citric acid/epsom salt | 0.1 | 1.0 | 7.8 | 1 hour | fast | fast | none |
| citric acid | 1 | 0 | 5 | 1 hour | fast | fast | none |
| citric acid/epsom salt | 1 | 2 | 4.5 | 1 hour | fast | fast | none |

Table 3 shows the results of talc formulations with citric acid and/or epsom salts. All the formulations tested in this Example had a relatively quick makedown, but failed to stay in suspension during the resting phase of the experiment.

Example 4

This Example describes the wet-out and dispersion characteristics of talc formulations of the present invention. The additives tested are EDTA, sodium sulfate, and sodium stearate.

Experiments to determine makedown, settling, and curdling/flocculation were performed as described in Example 1. Talc formulations were prepared as described in Example 1. In this Example, additives tested were EDTA and/or sodium sulfate and/or sodium stearate.

TABLE 4

Talc formulations and makedown rate, settling rate, and suspension characteristics

| Formulation, name | wt. % EDTA | wt. % sodium sulfate | wt. % sodium stearate | pH | settling time | makedown rate | settling rate | curdled or flocculated? |
|---|---|---|---|---|---|---|---|---|
| Control | 0 | 0 | 0 | 8.5 | 1 hour | fast | fast | none |
| EDTA | 0.1 | 0.1 | 0 | 6.9 | 1 hour | fast | fast | none |
| EDTA | 0.2 | 1 | 0 | 7.2 | 1 hour | fast | fast | none |
| sodium sulfate | 0 | 0.5 | 0 | 8.5 | 1 hour | fast | fast | none |
| sodium stearate | 0 | 0 | 0.5 | 8.5 | 0.75 hour | fast | fast | none |

Table 4 shows the results of talc formulations with EDTA, sodium sulfate, and sodium stearate. All the formulations tested in this Example had a relatively quick makedown, but failed to stay in suspension during the resting phase of the experiment.

Example 5

This Example describes the wet-out and dispersion characteristics of talc formulations of the present invention. The additives tested are alum and citric acid.

Experiments to determine makedown, settling, and curdling/flocculation were performed as described in Example 1. Talc formulations were prepared as described in Example 1. In this Example, additives tested were alum (aluminum sulfate) and/or citric acid.

TABLE 5

Talc formulations and makedown rate, settling rate, and suspension characteristics

| Formulation, name | wt. % alum | wt. % citric acid | pH | settling time | makedown rate | settling rate | curdled or flocculated? |
|---|---|---|---|---|---|---|---|
| Control | 0 | 0 | 8.5 | 1 hour | fast | fast | none |
| Alum | 0.2 | 0 | 7.1 | 0.75 hour | fast | fast | none |
| Alum | 0.4 | 0 | 6.9 | 1 hour | fast | fast | none |
| alum/citric acid | 0.2 | 0.1 | 7.5 | 1 hour | fast | fast | none |
| alum/citric acid | 0.4 | 0.1 | 7.2 | 1 hour | fast | fast | none |
| Alum/citric acid | 0.5 | 0.5 | 6.9 | 16 hour | fast | fast | none |

Table 5 shows the results of talc formulations with alum and/or citric acid. All the formulations tested in this Example had a relatively quick makedown, but failed to stay in suspension during the resting phase of the experiment.

Example 6

This Example describes the wet-out and dispersion characteristics of talc formulations of the present invention. The additives tested are soda ash, alum, corn starch, and citric acid.

Experiments to determine makedown, settling, and curdling/flocculation were performed as described in Example 1. Talc formulations were prepared as described in Example 1.

TABLE 6

Talc formulations and makedown rate, settling rate, and suspension characteristics

| additives (wt % of total wt) | pH | settling time | makedown rate | settling rate | curdled or flocculated? |
|---|---|---|---|---|---|
| none (control) | 8.5 | 1 hour | fast | fast | none |
| corn starch, 0.05% | 8.4 | 1 hour | fast | slow | flocculated |
| epsom salt, 1.0% 0.2% citric acid | 7.7 | 1 hour | slow | fast | unknown |
| 0.4% alum | 7.3 | 1 hour | fast | fast | unknown |
| 2% epsom salt | 8.1 | 1 hour | slow | fast | unknown |
| 0.4% alum 0.4% epsom salt | 7.9 | 1 hour | fast | fast | unknown |

Table 6 shows the results of talc formulations with soda ash, alum, citric acid, Epsom salts, or combinations.

Example 7

This Example describes the wet-out and dispersion characteristics of talc formulations of the present invention. The additives tested are alum, guar gum, and Epsom salts.

Experiments to determine makedown, settling, and curdling/flocculation were performed as described in Example 1. Talc formulations were prepared as described in Example 1.

TABLE 7

Talc formulations and makedown rate, settling rate, and suspension characteristics

| Formulation, name | additives (wt % of total wt) | pH | settling time | makedown rate | settling rate | curdled or flocculated? | leaf wetting |
|---|---|---|---|---|---|---|---|
| Control | none | 8.5 | 1 hour | fast | fast | none | poor |
| 042803A | alum, 0.2% Epsom salts 0.2% | N.d. | 1 hour | slow | ? | ? | good |
| 042803D | soda ash, 0.2% Alum, 0.2% | 8.4 | 1 hour | fast | ? | ? | good |
| SURROUND ™ | | 9.7 | 1 hour | fast | medium | flocculated | good |

Table 7 shows the results of talc formulations with soda ash, alum, citric acid, epsom salts, or combinations. Formulations 042503B-E all had a fast makedown and a slow settling rate, resulting in a suspension with flocculated talc.

Example 8

This Example describes the preparation of a crop protectant formulation of the present invention in pellet form.

A formulation is made by preparing a salt water premix of 531.6 pounds of water, 2.8 pounds of citric acid, and 5.2 pounds of Epsom salt (magnesium sulfate heptahydrate). To this mix, 50 pounds of soda ash is added. The resulting solution is then mixed with talc in a solution:talc weight ratio of 21:79. Talc had been pretreated to create a Mistron Vapor powder (finely ground talc). This formulation had a pH of about pH 10.4 to about 10.5. The complete formulation was then pelletized and dried in a 200° C. oven to a moisture level of less than 5% (target 3% moisture).

Pellets of this formulation disperse quickly and completely to form a slurry in water. When pellets of this formulation are added to water to create a slurry, the slurry settled slowly to a rather firm sediment. However, gentle shaking or stirring restored the slurry.

Example 9

This Example describes the appearance of a slurry of the present invention after its application onto tree leaves.

A slurry was prepared as described in Example 8. The slurry, as well as a SURROUND control, was sprayed onto ash tree leaves in an amount and in a manner as recommended by the SURROUND product insert and allowed to dry. Gross observation of the sprayed leaves showed that the appearance of the formulation of Example 8 on the leaves is almost identical to that of SURROUND sprayed onto ash tree leaves as a control. Better uniformity of coating on the ash tree leaves as compared to SURROUND was observed. Observation under a microscope shows a nearly identical type of attachment and coating on the leaf surface as observed for the SURROUND control sprayed leaf.

Example 10

This Example describes the appearance of a slurry of the present invention after its application onto apples.

Ripened Granny Smith-type apples (coated with alar wax, obtained from an retail grocery store) were sprayed with SURROUND and the formulation described in Example 8 as described in Example 9 and allowed to dry. Gross observation of the sprayed apples showed that significantly better uniformity of coating (increased wetting) was observed on the formulation of Example 8-sprayed apple compared to the SURROUND sprayed apple.

Example 11

This Example describes the behavior of insects and nymphs on ash trees after spraying with a formulation of the present invention.

(A) Nymphs. Clusters of microscopic nymphs (aphid) were observed on an ash tree. These nymphs had an oily or wet skin. After spraying the clusters with a formulation described in Example 8 in the manner described in Example 9, the nymphs became immobilized and dried up within a day. For mobile nymphs, sprayed leaf surfaces appear to transfer the talc formulation to the insect's body parts causing the injuries as described previously.

(B) Adult aphids. Aphids present on an ash tree leaf were sprayed with a formulation described in Example 8 in the manner described in Example 9, and were compared to unsprayed aphids on the same ash tree. After spraying, various areas of the abdomen, legs, and thorax of the aphids were observed to be coated with talc. Unlike the control unsprayed insects, the sprayed insects were seen to continuously scrape their coated body parts but were not successful in removing the talc agglomerates. Ants that were harvesting the aphids for their juices left the area. The next day, the sprayed aphids were observed to have left the sprayed leaves and had migrated to the unsprayed leaves.

The sprayed aphids which had migrated to the sprayed leaves still had talc on them. Most of the sprayed aphids had sprouted wings, but the wings appeared to be deformed, likely from the drying action of the talc. However, only one of the control aphids had sprouted wings. Possibly, in addition to deforming wings, the formulation may have also induced premature molting.

The principles, preferred embodiments and modes of operation of the present invention have been described in the foregoing specification. The invention which is intended to be protected herein should not, however, be construed as limited to the particular forms disclosed, as these are to be regarded as illustrative rather than restrictive. Variations and changes may be made by those skilled in the art without departing from the spirit of the present invention. Accordingly, the foregoing best mode of carrying out the invention should be considered exemplary in nature and not as limiting to the scope and spirit of the invention as set forth in the appended claims.

What is claimed is:

1. A composition, for application to crops, comprising:
talc;
citric acid;
magnesium sulfate heptahydrate; and
soda ash,
wherein the composition is in pellet form.

2. The composition of claim 1, wherein the talc comprises between about 50 dry wt. % and about 99.9 dry wt. %.

3. The composition of claim 1, wherein the talc comprises about 97 dry wt. %.

4. The composition of claim 1 wherein the composition comprises between about 500 ppm to about 2000 ppm citric acid.

5. The composition of claim 1, wherein the composition comprises between about 1000 ppm to about 1250 ppm citric acid.

6. The composition of claim 1, wherein the magnesium sulfate heptahydrate is added in the amount of between about 1000 ppm to about 4000 ppm.

7. The composition of claim 1, wherein the magnesium sulfate heptahydrate is added in the amount of between about 2000 ppm to about 3000 ppm.

8. The composition of claim 1, wherein the magnesium sulfate heptahydrate is added in the amount of about 2500 ppm.

9. The composition of claim 1, wherein the citric acid and the magnesium sulfate heptahydrate are present in a ratio of between about 1:0.5 to about 1:10 citric acid:magnesium sulfate heptahydrate.

10. The composition of claim 1, further comprising an oil.

11. The composition, as claimed in claim 1 wherein the talc is present in an amount between about 75 dry wt. % to about 99 dry wt. %, the citric acid is present in an amount between about 500 ppm and about 2000 ppm, the magnesium sulfate heptahydrate is present in an amount between about 1000 ppm and about 4000 ppm and the soda ash is present in an amount between about 1 dry wt. % and about 4 dry wt. %.

12. The composition, as claimed in claim 1, wherein the talc is present in an amount of about 97.125 dry wt. %, the citric acid is present in an amount of about 0.125 dry wt. %, the magnesium sulfate heptahydrate is present in an amount of about 0.25 dry wt. %, and the soda ash is present in an amount of about 2.5 dry wt. %.

13. A method for crop protection, comprising applying to at least a portion of a surface of a crop an effective amount of a slurry composition, comprising the composition of claim 1 and water
wherein the slurry composition has a pH of between about 9.0 and about 11.6.

14. The method of claim 13 wherein the step of applying is performed by a process selected from the group consisting of spraying, painting, and dipping.

15. The method of claim 13 wherein the crop is selected from the group consisting of fruits, vegetables, grains, legumes, trees, shrubs, flowers, grasses, roots, landscape plants, ornamental plants, and crop plants.

16. A method for protecting crops from freezing, comprising applying to at least a portion of a surface of a crop an effective amount of a slurry composition, comprising the composition of claim 1 and water
wherein the slurry composition has a pH of between about 9.0 and about 11.6.

17. The method of claim 16, wherein the method is conducted in combination with another freeze protection technique.

18. The method of 17, wherein the other freeze protection technique is selected from covering plants and burning smudge pots.

19. A method for protecting crops from pest infestation, comprising applying to at least a portion of a surface of a crop an effective amount of a slurry composition, comprising the composition of claim 1 and water
wherein the slurry composition has a pH of between about 9.0 and about 11.6.

* * * * *